United States Patent [19]

Iwasaki

[11] 3,949,600

[45] Apr. 13, 1976

[54] LOAD APPLICATION MECHANISM OF ROCKWELL HARDNESS TESTER

[75] Inventor: Shozo Iwasaki, Ebina, Japan

[73] Assignee: Kabushiki Kaisha Akashi Seisakusho, Japan

[22] Filed: Dec. 12, 1974

[21] Appl. No.: 531,977

[30] Foreign Application Priority Data

Dec. 20, 1973 Japan............................ 48-143272

[52] U.S. Cl. ................................................... 73/83
[51] Int. Cl.² ............................................. G01N 3/44
[58] Field of Search............................ 73/78, 81, 83

[56] References Cited
UNITED STATES PATENTS

| | | | |
|---|---|---|---|
| 1,516,208 | 11/1924 | Rockwell................................ | 73/83 |
| 2,813,420 | 11/1957 | Miller..................................... | 73/83 |

*Primary Examiner*—James J. Gill
*Attorney, Agent, or Firm*—Robert E. Burns; Emmanuel J. Lobato; Bruce L. Adams

[57] ABSTRACT

A Rockwell hardness tester having a load application mechanism having a load transfer unit divided into an upper transfer member and a lower transfer member having bores through which an indenter shaft of the tester extends axially with some play. The transfer members are disposed coaxially and have a pair of balls therebetween horizontally arranged in a direction perpendicular to a knife edge on an upper end of the upper transfer member supporting a load application lever. The load transfer unit rests on a spring support cylinder with an initial load spring circumferentially thereof and having its lower convolutions resting on the expanded portion of the indenter shaft and the load applied to the tester is accordingly never applied eccentrically to the indenter shaft.

3 Claims, 5 Drawing Figures

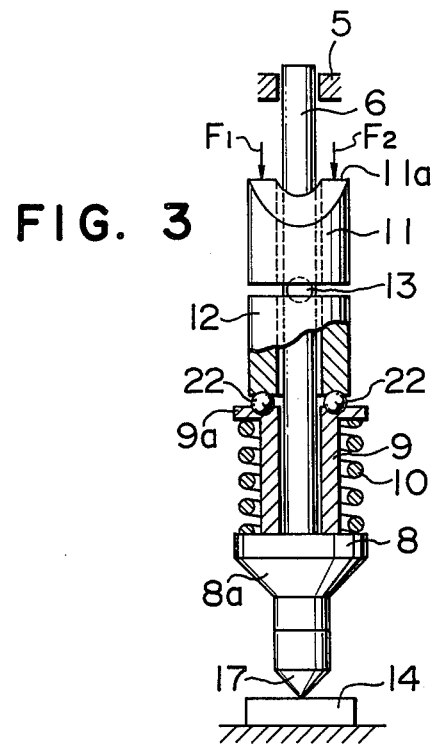
FIG. 3
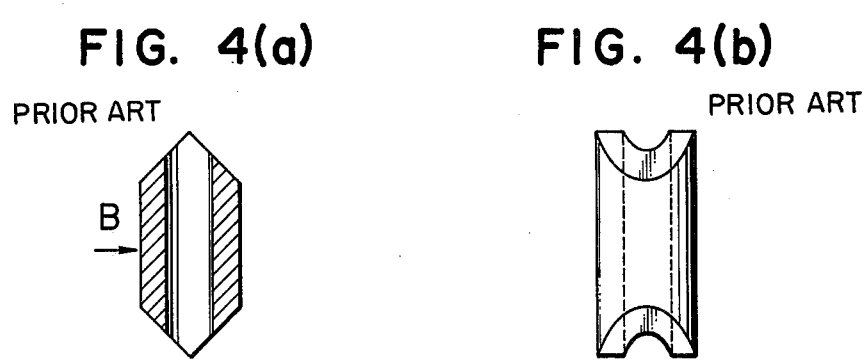
FIG. 4(a) PRIOR ART
FIG. 4(b) PRIOR ART

LOAD APPLICATION MECHANISM OF ROCKWELL HARDNESS TESTER

BACKGROUND OF THE INVENTION

The present invention relates to a load application mechanism of the Rockwell hardness tester. More in particular, it relates to a load application mechanism that permits smooth transfer of load from a load application level to an indenter shaft without difficulty.

Conventionally, the load application mechanism of such type has been popularly used, in which transfer of load from the load application level to the spring support cylinder on the indenter shaft is conducted through a monobloc load transfer member with parallel knife edges formed along its upper and lower ends. With this type of conventional load application mechanism, it is difficult to work the knife edges and their receivers with a high degree of accuracy. Consequently, error may arise in load or displacement of the pressure shaft, under the effect of an eccentric load imposed on the indenter shaft.

Then it becomes conceivable to apply to the load application mechanism of a Rockwell hardness tester, an idea of interposing a load transfer member having an upper and a lower knife edge and a universal joint between the load application level and the indenter shaft, as described in the Official Patent Gazette No. 39-16495. However, this type of system also involves several problems. It still requires high-precision work to insure the parallelism of the knife edges formed along the upper and lower ends of the load transfer member. The universal joint must be prepared with high accuracy, too.

SUMMARY OF THE INVENTION

An object of this invention is to offer a solution to these problems; that is, to provide a load application mechanism of the Rockwell hardness tester that is capable of being worked easily and producing a high degree of load accuracy.

To attain this object, the load application mechanism according to this invention features a rockwell hardness tester comprising a load application lever swingably fitted to the Rockwell hardness tester proper, an indenter shaft whose upper portion is inserted in a guide hole formed in said lever and lower portion in a stopper hole in said tester proper, an initial load spring interposed between an expanded portion of said indenter shaft for engagement with said stopper hole and a spring support cylinder playably engaged with said indenter shaft, and a load transfer unit disposed between the lower edge of said guide hole and the upper end of said spring support cylinder, a load application mechanism wherein said load transfer unit consists of an upper transfer member and a lower transfer member, both of which are cylindrically shaped and playably engaged with said indenter shaft, a knife edge formed along the upper edge of said upper transfer member is supported by a knife edge support at the lower end of said guide hole, and said upper and lower transfer members are held in contact with each other, with a pair of balls, horizontally arranged in a direction perpendicular to said knife edge, therebetween.

In this load application mechanism of the Rockwell hardness tester according to the present invention, the load transfer unit between the load application lever and the spring support cylinder on the indenter shaft is divided into upper and lower transfer members. Between these transfer members are interposed a pair of load transferring balls horizontally arranged in a direction perpendicular to the knife edge along the upper end of the upper transfer member. Load is very accurately transferred, without involving eccentric loading through these balls and the upper and lower transfer members. This arrangement requires much less precision work than the conventional type in which parallel knife edges are formed along the top and bottom ends of a monobloc load transfer member.

Another feature of the load application mechanism of the Rockwell hardness tester according to the invention is that the lower end of the lower transfer member and the upper end of the spring support cylinder are held in contact with each other, with a second pair of balls, horizontally arranged perpendicular to the direction in which the first pair of balls are disposed.

This provision of the second pair of balls between the lower transfer member and the spring support cylinder, perpendicular to the arrangement direction of the load transfer balls between the upper and lower transfer members is conducive to further reducing difficult work and increasing the accuracy with which load is transferred.

BRIEF DESCRIPTION OF THE DRAWINGS

FIG. 3 is a view similar to FIG. 2, but showing another embodiment of this invention.

FIG. 4(a) is a cross-sectional view showing a load transfer unit of the conventional load application mechanism.

FIG. 4(b) is a view as seen in the direction of the arrow B in FIG. 4(a).

DESCRIPTION OF THE PREFERRED EMBODIMENTS

Figure 1:
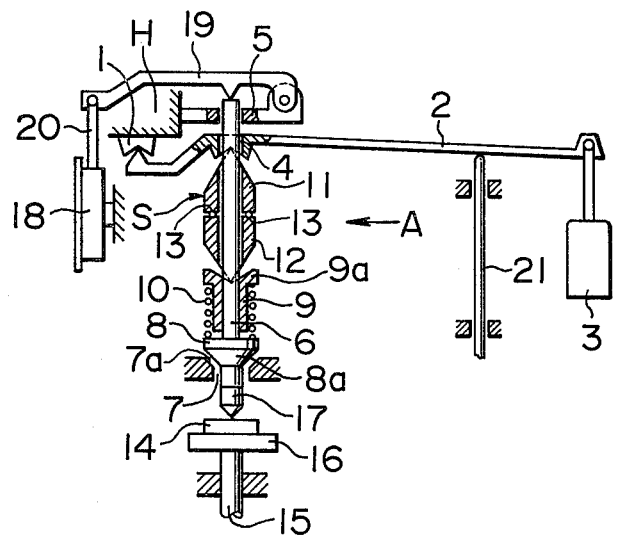
FIG. 1 is a cross-sectional view of an embodiment, showing the load application mechanism of the Rockwell hardness tester according to this invention.
Figure 2:
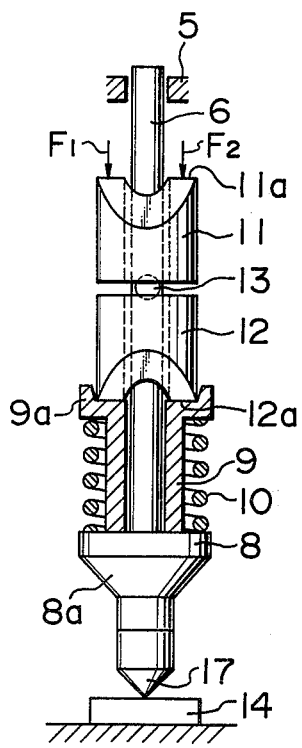
FIG. 2 is a partial sectional view, looking in the direction of the arrow A in FIG. 1.

Now embodiments of this invention will be described with reference to the accompanying drawings. FIG. 1 is a cross-sectional view showing a first embodiment of load application mechanism of a Rockwell hardness tester according to this invention. FIG. 2 is a partial sectional view, looking in the direction of the arrow A in FIG. 1. A load application lever 2 is disposed so that it is swingable with respect to a tester proper H on a fulcrum 1. The end of this load application lever 2 opposite to the fulcrum 1 is adapted to hang a weight 3.

The upper portion of an indenter shaft 6 is passed through a guide hole 4 formed in the load application lever 2 and the guide member 5 fixed to the tester proper H. While the lower portion of the indenter shaft 6 is passed through a stopper hole 7 formed in the tester proper. By this means, the indenter shaft 6 is guidedly moved up and down.

In addition, an expanded portion 8 is formed on the indenter shaft 6, which has a conical surface 8a adapted to fit in an inverse conical cut 7a in the stopper hole 7. Then, an initial load spring 10 is interposed between an upper flange portion 9a of a spring support cylinder 9 playably engaged with the indenter shaft 6 and the expanded portion 8.

Also, a load transfer unit S is interposed between the lower end of the guide hole 4 in the load application lever 2 and the upper flange portion 9a of the spring support cylinder 9.

This load transfer unit S is made up of an upper transfer member 11 and a lower transfer member 12, both cylindrically shaped and axially displaceable on the indenter shaft 6. A knife edge 11a formed along the upper end of the upper transfer member 11 is received by a knife edge support formed at the lower end of the guide hole 4.

Between the upper and lower transfer members 11 and 12, there are horizontally arranged a pair of balls 13 for transferring the load, in a direction at right angles with the knife edge 11a. These balls 13 are held in depressions in order to prevent their dropping.

Also, a knife edge 12a formed along the lower end of the lower transfer member 12 is received by a knife edge support formed at the upper end of the spring support cylinder 9.

For measuring the Rockwell hardness of a specimen 14, it is pushed up, together with a specimen anvil 16, by a support shaft 15, until the specimen 14 comes in contact with an indenter 17 at the lowest end of the indenter shaft 6. By further raising, the conical surface 8a on the expanded portion 8 of the indenter shaft 6 becomes detached from the inverse conical surface 7a in the stopper hole 7.

Then, the indicator of a dial gage 18 is adjusted to the reference division while there is a suitable clearance between the lower end of the spring support cylinder 9 and the expanded portion 8 of the indenter shaft 6.

The dial gauge 18 is operated through an enlarging or magnifying lever 19 that contacts the upper end of the indenter shaft 6 and a spindle 20 pivotally fitted thereto.

By then lowering a control shaft 21, the load application lever 2 is turned on the fulcrum 1, and the upper transfer member 11 is depressed. As a consequence, the balls 13, the lower transfer member 12 and the spring support cylinder 9 are lowered, too, as illustrated in FIG. 2. This brings the lower end of the spring support cylinder 9 in contact with the expanded portion 8 of the indenter shaft 6, and causes the control shaft 21 to separate from the load application lever 2. Then, a test load is completely applied on the indenter shaft 6.

By elevating the control shaft 21 to the original position after thus applying the test load, the test load is released and only the force of the initial load spring 10 works on the indenter shaft 6, as shown in FIG. 1.

Under this condition, a hardness indicated on the dial gauge 18 can be read. That is, the Rockwell hardness is determined from the depth of impression of the indenter 17 on being applied the test load.

In the conventional load application mechanism of the Rockwell hardness tester, a part that corresponds to the above-described load transfer unit S is made in one piece, as shown in FIGS. 4(a) and (b). And parallel knife edges are formed along the upper and lower ends of such monobloc member. With this type of design, a high degree of working and assembling accuracy in insuring parallelism of the two knife edges and their receiving grooves. If such accuracy is not perfectly satisfied, an eccentric load will be imposed on the indenter shaft when transferring the load, which may in turn produce errors in the load and the displacement of the indenter shaft.

In contrast, the load application mechanism of this invention has the load transfer unit S that is divided into the upper and lower transfer members 11 and 12, with the pair of balls 13 interposed therebetween, as described previously. Besides, these balls 13 are arranged in a direction perpendicular to the knife edge 11a at the top end of the upper transfer member 11. Therefore, the upper and lower transfer members 11 and 12 swingingly move on the balls 13 until the loads $F_1$ and $F_2$ applied on both sides of the knife edge 11a on the upper transfer member become automatically balanced with respect to the center axis between the two balls 13, as shown in FIG. 2. This permits smooth transfer of the load, without causing an eccentric load. This also prevents the knife edge 12a of the lower transfer member from eccentrically touching the knife edge receiver at the top end of the spring support cylinder 9.

As understood from the above, the first embodiment shown in FIGS. 1 and 2 assures very accurate load transfer, through the pair of balls 13 interposed between the upper and lower transfer members 11 and 12 that make up the load transfer unit S.

FIG. 3 is a view similar to FIG. 2, but showing a second embodiment of this invention. In both figures, similar reference characters designate similar parts.

In this second embodiment of FIG. 3, another pair of load transfer balls 22 are disposed between the lower transfer member 12 and the upper end of the spring support cylinder 9. These balls are disposed in a direction that is at right angles with that of the first pair of balls 13.

The load transfer unit S of this second embodiment possesses only one knife edge 11a at the top end of the upper transfer member 11, which reduces complexity of work to a great extent. Well-balanced load transfer is effected through the perpendicularly arranged first pair of balls 13 and second pair of balls 22. No eccentric load is imposed on the indenter shaft 6, thus eliminating the possibility of producing errors in the load and the displacement of the indenter shaft.

Of course, the second pair of balls 22 are held in depressions in order to prevent their coming off, as well.

As has been fully described, the load application mechanism of the Rockwell hardness tester according to this invention offers a structure easy to manufacture, insures highly accurate transfer of load, and thereby makes it possible to measure the accurate Rockwell hardness.

What is claimed is:

1. In a Rockwell hardness tester: a load application lever swingably mounted, and having a guide hole, an indenter shaft having an upper portion inserted in said guide hole formed in said lever and a lower portion in a stopper hole, stopper means defining said stopper hole, said indenter shaft having an expanded portion which limits axial travel of said indenter shaft by engagement with said stopper means, a spring support cylinder circumferentially of said indenter shaft loosely fitted thereabout, an initial spare load spring resiliently supporting said spring support cylinder on said indenter shaft in the absence of an initial load and interposed between said expanded portion of said indenter shaft for engagement with said stopper hole and said spring support cylinder, a load application mechanism comprising a load transfer unit disposed between a lower edge of said guide hole and the upper end of said spring support cylinder, said load transfer unit comprising an upper transfer member and a lower transfer member cylindrically shaped disposed circumferentially relatively loosely about said indenter shaft, a knife edge at a lower end of said guide hole, a knife edge along an upper end of said upper transfer member supporting said knife edge support at the lower end of said guide hole, and a pair of balls between said upper and lower transfer members held in contact therewith, and said pair of balls being horizontally arranged in a direction perpendicular to said knife edge, therebetween.

2. In a Rockwell hardness tester according to claim 1, including a second pair of balls disposed between a lower end of said lower transfer member and an upper end of said spring support cylinder to maintain them in contact with each other, and said second pair of balls being disposed horizontally arranged perpendicular to the direction in which said first pair of balls are disposed.

3. In a Rockwell hardness tester having an axially displaceable indenter shaft and a swingable lever for supporting an initial load thereon for application to the indenter shaft, a load transfer mechanism for applying said initial load to the indenter shaft without eccentricity comprising, a load transfer unit disposed circumferentially of said indenter shaft, said load transfer unit comprising two coactive transfer members constituting an upper transfer member and a lower transfer member, a knife edge on an upper end of the upper transfer member for supporting said lever thereon, a pair of balls between the transfer members holding them axially spaced and constantly in contact therewith, said balls being arranged horizontally in a direction perpendicular to said knife edge, said transfer members having axial bores through which indenter shaft extends axially with some play for axial movement relative thereto, said indenter shaft having an expanded portion, a spring-support cylinder supporting said load transfer unit, an initial load spring wound about said spring support cylinder resiliently supporting said spring-support cylinder on said indenter shaft in the absence of an initial load and having a convolution resting on said expanded portion for resiliently supporting said spring-support cylinder.

* * * * *